United States Patent [19]

Matsuda et al.

[11] Patent Number: 4,518,810

[45] Date of Patent: May 21, 1985

[54] PROCESS FOR PREPARATION OF GUERBET ALCOHOLS

[75] Inventors: Morio Matsuda; Masamitsu Horio, both of Wakayama, Japan

[73] Assignee: Kao Corporation, Tokyo, Japan

[21] Appl. No.: 473,918

[22] Filed: Mar. 10, 1983

[30] Foreign Application Priority Data

Mar. 18, 1982 [JP]  Japan ................................. 57-43370

[51] Int. Cl.³ ............................................. C07C 29/34
[52] U.S. Cl. ................................... 568/905; 568/807; 568/816
[58] Field of Search ......................................... 568/905

[56] References Cited

U.S. PATENT DOCUMENTS 2,762,847  9/1956  Miller et al. ......................... 568/905
2,836,628  5/1958  Miller ................................... 568/905
2,862,013  11/1958  Miller et al. ......................... 568/905

*Primary Examiner*—J. E. Evans
*Attorney, Agent, or Firm*—Flynn, Thiel, Boutell & Tanis

[57] ABSTRACT

A Guerbert alcohol is effectively and selectively obtained by heating a primary alcohol in the presence of an alkaline substance and a copper-nickel catalyst in which a weight ratio of copper to nickel is in the range of from 1:9 to 9:1.

4 Claims, No Drawings

PROCESS FOR PREPARATION OF GUERBET ALCOHOLS

The invention relates to a process for preparing a Guerbet alcohol, that is, branched dimerized alcohol, by dehydrogenating and condensing a primary alcohol.

It is well-known that when a primary alcohol is condensed by heating in the presence of an alkali alone or together with a co-catalyst, one molecule of water is removed from two molecules of the starting alcohol to obtain one molecule of a branched dimerized alcohol, and this reaction is called the "Guerbet reaction". Various reports have been published in connection with the mechanism of the Guerbet reaction, and it has been considered that this reaction is advanced according to the following mechanism:

$$2RCH_2CH_2OH \longrightarrow 2RCH_2CHO \quad (1)$$

$$2RCH_2CHO \longrightarrow R-CH_2CH=\underset{\underset{R}{|}}{C}-CHO + H_2O \quad (2)$$

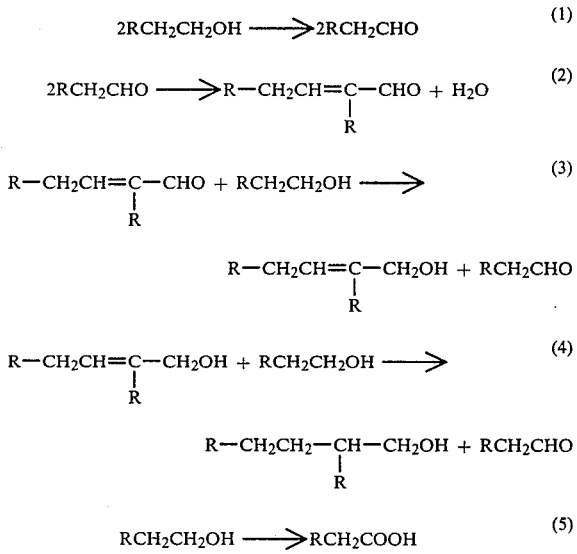

$$RCH_2CH_2OH \longrightarrow RCH_2COOH \quad (5)$$

It is considered that the branched dimerized alcohol is formed by the concurrent reactions represented by the above formulae (1) through (4). Rates of the reactions represented by the formulae (1) through (4) vary according to the reaction temperature, the amount of the alkali and the amount and kind of the co-catalyst, and hence, the selectivity should naturally vary depending on these factors. The reaction represented by the formula (5) is a reaction of consuming the starting alcohol, and as the reaction temperature is elevated, the rate of this reaction is ordinarily increased, that is, the yield of the branched dimerized alcohol is reduced. Accordingly, examinations have been made on cocatalysts for inhibiting the advance of the reaction of the formula (5) while promoting those of the formulae (1) through (4). For example, copper chromite, copper-zinc oxide, copper powder, zinc oxide, zinc chromite, stabilized nickel, nickel supported on alumina silicate or active carbon, platinum supported on alumina silicate or active carbon, palladium supported on alumina silicate or active carbon, ruthenium supported on alumina silicate or active carbon, rhodium supported on alumina silicate or active carbon, and Raney catalysts (nickel, chromiun, copper and the like) and developed catalysts thereof have been used as the co-catalyst.

However, these co-catalysts are still insufficient in the point of increasing the rates of the reactions of the formulae (3) and (4) and eventually obtaining a Guerbet alcohol having a high quality. When the foregoing co-catalysts are employed, the reactions of the formulae (1) and (2) are promoted and the conversion is increased, but formation of aldehydes, unsaturated compounds and carboxylic acids as by-products is increased, resulting in reduction of the yield and selectivity.

The aldehyde and unsaturated compounds formed as by-products have a bad smell and cause discoloration and oxidation, and these by-products impede applications of the branched dimerized alcohol.

We have made researches with a view to preparing a Guerbet alcohol having a high quality with a reduced content of aldehyde and unsaturated compounds as by-products and preventing reduction of the yield by controlling formation of carboxylic acid salts as by-products, and as the result, found that this object can be attained by condensing by heating primary alcohol represented by the following formula [I]:

$$R-CH_2-CH_2-OH \quad [I]$$

wherein R stands for a group selected from the group consisting of an alkyl group having 1 to 24 carbon atoms, a cycloalkyl group, an aryl group and an aralkyl group, in the presence of an alkaline substance and a copper-nickel catalyst. We have now completed the present invention based on this finding.

To our great surprise, when the copper-nickel catalyst is used in the above-mentioned reaction, the reactivity per unit metal weight is several times as high as those of the known copper chromate and Raney nickel catalysts and this catalyst exerts a catalytic action on the reactions of the formula (3) and (4) and a branched dimerized alcohol having a reduced content of the aldehyde and unsaturated compounds can be obtained.

Furthermore, since the reaction rate is increased, the reaction may be carried out at lower temperatures, and if the reaction temperature is controlled to a low level, formation of a carboxylic acid salt as a by-product is reduced and the alkali of the catalyst effectively acts mainly on the main reaction. Moreover, the post-treatment for removing the carboxylic acid salt can be performed very easily.

The copper-nickel catalyst which has been used in the present invention may be recovered and then used for the reaction again.

The copper-nickel catalyst used in the present invention comprises copper and nickel components as indispensible components, and these components may be used in the form of metals or metal oxides or in the state thereof supported on a suitable carrier.

Materials customarily used as catalyst carriers, such as alumina, silica-alumina, diatomaceous earth, silica, active carbon, natural zeolite and artificial zeolite may be used as the carrier in the process of the present invention. The amount of the catalytic metals supported on the carrier is not particularly critical, but it is ordinarily preferred that the amount of the catalytic metals supported on the carrier be 10 to 60 percent by weight.

The catalyst may be prepared according to various methods. For example in the case where the catalytic metal components are supported on a carrier, there may be adopted a method in which a carrier is incorporated into a solution of appropriate salts of copper and nickel to be sufficiently impregnated with the solution, then dried and calcined (the impregnation method), and a method in which a carrier is incorporated in an aqueous solution of appropriate salts of copper and nickel, for example, an aqueous solution of copper nitrate and nickel nitrate, the solution is sufficiently stirred and an aqueous solution of an alkali such as sodium carbonate, aqueous ammonia or sodium hydroxide is added to the above solution to precipitate metal salts on the carrier (the coprecipitation method). In the case where zeolite or the like is used as the carrier, there may be adopted a method in which sodium or the like on zeolite is ion-exchanged with copper and nickel (the ion exchange method). Furthermore, there may be adopted a method in which copper, nickel and aluminum metals are melted by heating, the melt is then cooled and solidified to form an alloy and aluminum in the alloy is eluted out by caustic soda (the alloy method). Namely, the catalyst may be prepared according to any of these known methods. In case of the impregnation and coprecipitation methods, the metal-deposited carrier is sufficiently washed with water, dried at about 100° C. and calcined at 300° to 400° C. to obtain a catalyst.

The copper-nickel catalyst used in the present invention is especially effective when the copper/nickel weight ratio is in the range of from 10/90 to 90/10, particularly in the range of from 85/15 to 50/50.

The copper and nickel catalyst to be used in the invention is characterized in that the reaction rate is increased to a level several times as high as that attained by a catalyst composed solely of copper or nickel. Moreover, the copper-nickel catalyst of the present invention is excellent in the rate of the Guerbet reaction over the conventional known co-catalysts.

Moreover, the copper-nickel catalyst of the present invention is characteristic over the known co-catalysts in that the copper-nickel catalyst is excellent in both the reaction rate and the selectivity. In short, the copper-nickel catalyst of the present invention is characterized in that the catalyst gives a Guerbet alcohol having a reduced content of by-products such as aldehyde or unsaturated compounds.

When the copper-nickel catalyst of the present invention is used, the above-mentioned effects can be attained under the same conditions as adopted for the conventional co-catalysts, and in the view of the specific characteristics, it is preferred that the reaction temperature be lowered. Namely, a reaction temperature lower than 250° C., especially lower than 230° C., is preferably selected.

When the catalyst of the present invention is not used or when a conventional co-catalyst is used, it is indispensable that the reaction should be carried out at a reaction temperature of 250° to 280° C. for 2 to 3 hours. When the copper-nickel catalyst of the present invention is used, a reaction temperature of 200° to 220° C. is sufficient if the reaction is conducted for the same time as described above. If the reaction temperature is thus lowered, formation of a carboxylic acid salt as a by-product is controlled and hence, the alkali of the catalyst acts effectively on the main reaction.

Any of primary alcohols represented by the above general formula [I] can be used as the starting alcohol in the present invention.

It is practicable in the invention that the process is conducted at 200° to 250° C. for 1 to 5 hours. Among the starting alcohol, a normal alkyl alcohol is suitably used. The cycloalkyl group as R of the formula has preferably 3 to 6 carbon atoms, especially cyclopentyl and cyclohexyl. The aryl group preferably includes phenyl. The aralkyl group preferably includes benzyl.

The reaction of the present invention is a dehydration reaction, and ordinarily, the reaction is advanced while water formed by the reaction is removed from the reaction system. For this purpose, there is usually adopted a method in which the dehydration reaction is carried out under reflux of the starting alcohol at a temperature higher than the boiling point of the starting alcohol. When the reaction temperature is lower than or different from the boiling point of the starting alcohol, the reaction is carried out under a reduced pressure or an elevated pressure. Furthermore, there may be adopted a method in which water formed by the reaction is expelled by blowing an inert gas such as nitrogen gas into the reaction system.

As the alkaline substance to be used in the present invention, there can be mentioned, for example, metallic sodium, sodium alcoholate, caustic soda, sodium carbonate, sodium amide, metallic potassium, potassium amide, potassium hydroxide, potassium carbonate and potassium phosphate. Among these alkaline substances, potassium hydroxide is especially preferred.

In the present invention, the alkaline substance may be used in an amount customarily adopted in the Guerbet reaction, but when the reaction temperature is relatively lowered by using the copper-nickel catalyst of the present invention, the proportion of the alkali to be consumed by conversion to an alkali salt of a carboxylic acid is reduced, and therefore, a sufficient catalytic action can be attained if the alkali is used in an amount corresponding to about ½ of the amount used in the conventional method. In short, in the present invention, the alkaline substance is used in an amount of 0.25 to 5% by weight, preferably 0.5 to 2.0% by weight, based on the starting alcohol.

An amount of the copper-nickel catalyst to be used as a co-catalyst in the invention is 0.002 to 1.0 percent by weight, preferably 0.005 to 0.2% by weight, based on the starting alcohol.

The present invention will now be described in detail with reference to the following Examples and Comparative Examples.

EXAMPLE 1

A 1-liter four-neck flask equipped with a stirrer, a thermometer, a nitrogen inlet and a condenser and separator for separating water formed by the reaction was charged with 505 g of 1-decanol having a purity of 99%, 7.5 g of granular potassium hydroxide and 0.05 g of a copper-nickel co-catalyst supported on alumina (the copper/nickel weight ratio was 80/20 and the total content of copper and nickel metals in the whole co-catalyst was 40% by weight). The temperature was elevated with bubbling nitrogen gas at a rate of 30 l/hr in the mixture through a flow meter. The time when the temperature was elevated to 220° C. was designated as the point of initiation of the reaction. The reaction was conducted at 220° C. until formation of water by the reaction stopped. The reaction was terminated after 3 hours. The liquid reaction mixture was cooled and filtered to remove the co-catalyst and the precipitated potassium carboxylate and the filtrate was distilled under a reduced pressure. An amount of the obtained 2-octyl-1-dodecanol as the branched dimerized alcohol was 424.0 g, and the yield was 89.9% of the theoretical value and the selectivity 95.0%. The obtained 2-octyl-1-dodecanol had an iodine value (hereinafter referred to as "IV value") of 1.5 and a CHO concentration of 148 ppm.

COMPARATIVE EXAMPLE 1

The reaction was carried out under the same conditions as described in Example 1 except that the copper-nickel catalyst was not used. Even if the reaction was conducted for 10 hours, the reaction was not completed. The amount of 2-octyldodecanol-1 obtained by conducting the reaction for 10 hours was 356.8 g, and the yield was 75.6% of the theoretical value and the selectivity was 89.1%. The IV value was 5.0 and the CHO concentration was 189 ppm.

COMPARATIVE EXAMPLE 2

The reaction was carried out under the same conditions as described in Example 1 except that 0.05 g of a commercially available copper chromite catalyst was used instead of the copper-nickel catalyst. The reaction time was 8 hours, and the amount of obtained 2-octyldodecanol-1 was 377.6 g. The yield was 80% of the theoretical value and the selectivity was 85%. The IV value was 7.0 and the CHO concentration was 914 ppm.

COMPARATIVE EXAMPLE 3

The reaction was carried out under the same conditions as described in Example 1 except that 0.05 g of a Raney nickel catalyst (developed product) was used instead of the copper-nickel catalyst. About 10 hours were required for completion of the reaction. The amount of obtained 2-octyldodecanol-1 was 401.2 g, and the yield was 85% of the theoretical value and the selectivity was 86.3%. The IV value was 4.0 and the CHO concentration was 450 ppm.

EXAMPLE 2

The same reaction vessel as used in Example 1 was charged with 510 g of 1-octanol having a purity of 98%, 15 g of a 50 % aqueous solution of potassium hydroxide and 0.1 g of the same copper-nickel catalyst as used in Example 1, and the temperature was elevated while bubbling nitrogen gas at a rate of 30 l/hr in the reaction vessel through a flow meter. When the temperature had been elevated up to 180° to 190° C., reflux started. As the reaction was proceeding, the reaction temperature rose and reached 220° C. after 2 hours and 30 minutes. The reaction was further conducted for 1 hour at this temperature. The reaction mixture was cooled down and then filtered at a pressure of a few atms. G to remove the copper-nickel catalsyt and the precipitated potassium carboxylate. The filtrate was distilled under a reduced pressure. The amount of the obtained 2-hexyl-1-decanol was 430.4 g, and the yield was 91.0% of the theoretical value and the selectivity was 95.5%. The IV value was 1.6 and the CHO concentration was 122 ppm.

COMPARATIVE EXAMPLE 4

The reaction was carried out under the same conditions as described in Example 2 except that 0.1 g of a commercially available copper chromite catalyst and 0.3 g of commercially available active carbon were used instead of the copper-nickel catalyst. Reflux started at 180° to 190° C. and the reaction temperature rose as the reaction was proceeding. But it took six and half hours to increase the reaction temperature up to 200° C. The reaction was further conducted for 1 hour at 220° C. The post-treatment were performed in the manner as described in Example 2. An amount of the obtained 2-hexyl-1-decanol was 382.8 g, and the yield was 81.1% of the theoretical value and the selectivity was 86.3%. The IV value was 7.5 and the CHO concentration was 1320 ppm.

EXAMPLE 3

The same reaction vessel as used in Example 1 was charged with 505 g of 1-decanol having a purity of 99%, 7.5 g of granular potassium hydroxide and 0.05 g of a copper-nickel catalyst supported on silica (the copper/nickel weight ratio was 80/20 and the total content of copper and nickel metals in the whole catalyst was 40% by weight), and the procedures of Example 1 were repeated in the same manner. The reaction was completed over a period of 4 hours at 220° ° C. An amount of the obtained 2-octyl-1-dodecanol was 416.3 g, and the yield was 88.2% of the theoretical value and the selectivity was 94.2%. The IV value was 1.6 and the CHO concentration was 174 ppm.

EXAMPLE 4

The same reaction vessel as used in Example 1 was charged with 505 g of 1-decanol having a purity of 99%, 7.5 g of granular potassium hydroxide and 0.025 g of an unsupported copper-nickel catalyst (the copper/nickel weight ratio was 80/20 and the total content of copper and nickel metals in the whole catalyst was 77% by weight). The reaction was carried out under the same conditions as described in Example 1. The reaction was completed after 3 hours and 30 minutes. An amount of the obtained 2-octyl-1-dodecanol was 404.0 g, and the yield thereof was 85.6% of the theoretical value and the selectivity was 93.8%. The IV value was 1.6 and the CHO concentration was 189 ppm.

EXAMPLE 5

The same reaction vessel as used in Example 1 was charged with 505 g of 1-decanol having a purity of 99%, 7.5 g of granular potassium hydroxide and 0.05 g of a copper-nickel catalyst supported on an alumina carrier (the copper/nickel weight ratio was 20/80 and the total content of copper and nickel metal in the whole catalyst was 40% by weight). The reaction was carried out under the same conditions as described in Example 1, and 5 hours and 30 minutes were required for completion of the reaction. The amount of obtained 2-octyldodecanol-1 was 410.6 g, and the yield was 87.0% of the theoretical value and the selectivity was 94.5%. The IV value was 1.6 and the CHO concentration was 351 ppm.

COMPARATIVE EXAMPLE 5

The reaction was carried out under the same conditions as described in Example 5 except that 0.05 g of a copper catalyst supported on alumina (the catalytic metal was composed solely of copper and the content of the copper metal in the whole catalyst was 41% by weight) was used instead of the copper-nickel catalyst used in Example 5. Eight hours were required for completion of the reaction. The amount of obtained 2-octyldodecanol-1 was 373.3 g, and the yield was 79.1% of the theoretical value and the selectivity was 84.2%. The IV value was 7.2 and the CHO concentration was 870 ppm.

COMPARATIVE EXAMPLE 6

The reaction was carried out under the same conditions as described in Example 5 except that 0.05 g of a nickel catalyst supported on alumina (the catalytic metal was composed solely of nickel and the content of the nickel metal in the whole catalyst was 39%) was used instead of the copper-nickel catalyst used in Example 5. Ten hours were required for completion of the reaction. An amount of the obtained 2-octyl-1-dodecanol was 403.0 g, and a yield was 85.4% of the theoretical value and the selectivity was 85.5%. The IV value was 4.2 and the CHO concentration was 609 ppm.

EXAMPLE 6

The reaction was carried out in the same manner as described in Example 1 except that 516.5 g of stearyl alcohol (having a purity of 96.8%) was used as the starting alcohol. The amount of obtained 2-hexadecyl-1-eicosanol was 443.9 g, and the yield was 91.9% of the theoretical value and the selectivity was 96.2%. The IV value was 0.9 and the CHO concentration was 83 ppm.

EXAMPLE 7

The reaction was carried out under the same conditions as described in Example 1 except that a copper-nickel co-catalyst supported on alumina, in which the copper/nickel weight ratio was 50/50 and the total content of copper and nickel metals in the whole catalyst was 40% by weight, was used instead of the copper-nickel co-catalyst used in Example 1. The reaction time was 5 hours. An amount of the obtained 2-octyl-1-dodecanol was 405.1 g, and a yield was 85.9% of the theoretical value. The IV value was 2.5 and the CHO concentration was 218 ppm.

COMPARATIVE EXAMPLE 7

The reaction was carried out under the same conditions as described in Example 1 except that 0.05 g of a commercially available copper chromite catalyst and 0.15 g of active carbon were used instead of the copper-nickel co-catalyst used in Example 1. The reaction time was 5 hours, and an amount of the obtained 2-octyl-1-dodecanol was 382.5 g and the yield was 81.1% of the theoretical value. The IV value was 7.5 and the CHO concentration was 1281 ppm.

COMPARATIVE EXAMPLE 8

The reaction was carried out under the same conditions as described in Example 1 except that 0.04 g of a commercially available copper chromite catalyst and 0.01 g, in term of metallic nickel, of a Raney nickel catalyst were used instead of the copper-nickel co-catalyst used in Example 1. The reaction time was 8 hours. An amount of the obtained 2-octyl-1-dodecanol was 391.5 g and the yield was 83.0% of the theoretical value. The IV value was 4.2 and the CHO concentration was 821 ppm.

What is claimed is:

1. A process for preparing a branched dimerized alcohol, which comprises: heating a primary alcohol having the formula $$RCH_2CH_2OH$$

in which R is alkyl having 1 to 24 carbon atoms, at a reaction temperature in the range of from 200° to 230° C., in the presence of from 0.25 to 5% by weight of potassium hydroxide and from 0.005 to 0.2% by weight of a co-catalyst consisting essentially of copper and nickel supported on a catalyst carrier and wherein the weight ratio of Cu/Ni is from 85/15 to 50/50, both said percentages being based on the weight of said primary alcohol, and removing water, as it is formed, from the reaction mixture, and thereby converting said primary alcohol, at a high yield and a high selectivity, to a branched dimerized alcohol having the formula $$RCH_2CH_2CHCH_2OH.$$
$$|$$
$$R$$

2. A process as claimed in claim 1 in which the reaction time is from 1 to 5 hours.

3. A process as claimed in claim 2 in which the amount of said potassium hydroxide is from 0.5 to 2% by weight, based on the weight of said primary alcohol.

4. A process as claimed in claim 1 in which the reaction temperature is from 20020 to 220° C. and the reaction time is from 2 to 3 hours.

* * * * *

UNITED STATES PATENT AND TRADEMARK OFFICE
CERTIFICATE OF CORRECTION

PATENT NO. : 4,518,810
DATED : May 21, 1985
INVENTOR(S) : Morio Matsuda

It is certified that error appears in the above-identified patent and that said Letters Patent is hereby corrected as shown below:

Column 8, line 43; change "20020" to ---200°C---.

Signed and Sealed this

Thirty-first Day of December 1985

[SEAL]

Attest:

DONALD J. QUIGG

Attesting Officer

Commissioner of Patents and Trademarks